(12) United States Patent
Latypov et al.

(10) Patent No.: US 6,340,780 B1
(45) Date of Patent: Jan. 22, 2002

(54) METHOD OF PREPARING SALTS OF DINITROMETHANE

(75) Inventors: Nikolai Latypov, Tumba; Ulf Wellmar, Södra Sandby; Abraham Langlet, Stockholm, all of (SE)

(73) Assignee: Totalförsvarets Forskningsinstitut, Stockholm (SE)

( * ) Notice: Subject to any disclaimer, the term of this patent is extended or adjusted under 35 U.S.C. 154(b) by 0 days.

(21) Appl. No.: 09/856,465
(22) PCT Filed: Dec. 8, 1999
(86) PCT No.: PCT/SE99/02301
  § 371 Date: Jun. 7, 2001
  § 102(e) Date: Jun. 7, 2001
(87) PCT Pub. No.: WO00/34223
  PCT Pub. Date: Jun. 15, 2000

(30) Foreign Application Priority Data

Dec. 8, 1998 (SE) .............................................. 9804252

(51) Int. Cl.$^7$ .............................................. C07C 205/02
(52) U.S. Cl. ...................................................... 568/944
(58) Field of Search ......................................... 568/944

(56) References Cited

U.S. PATENT DOCUMENTS 3,067,261 A * 12/1962 Clark
4,233,249 A * 11/1980 Grakauskus
4,233,250 A * 11/1980 Grakauskus

* cited by examiner

*Primary Examiner*—Michael L. Shippen
(74) *Attorney, Agent, or Firm*—Jacobson Holman, PLLC

(57) ABSTRACT

A method of preparing dinitromethane salts usable as intermediate products add starting material for production of explosives and propellants. Substituted 1,2-diazoles, 1,2,4-triazoles or 1,3-diazines, such as barbituric acid, are nitrated to obtain a gem-dinitro group on a carbon atom in the heterocyclic ring. The product is hydrolysed to split off dinitromethane which is neutralised with a neutralising agent to obtain a corresponding salt of dinitromethane.

13 Claims, No Drawings

METHOD OF PREPARING SALTS OF DINITROMETHANE

The invention relates to dinitromethane, more specifically to a method of preparing dinitromethane in the form of its salt with an organic or inorganic cation.

Free dinitromethane is an instable yellowish oil which decomposes even at room temperature. Salts of dinitromethane, especially alkali metal salts, are stable compounds which have an important application as intermediate product and starting material for production of explosives and propellants containing gem-dinitro groups. Salts of dinitromethane can also be used as oxidiser in propellant compositions and pyrotechnic charges and in this application they have the advantage of being an oxidiser free from chlorine.

A method of synthesising alkali metal salts of dinitromethane is disclosed in U.S. Pat. No. 4,233,250. This prior-art method is begun by nitration of cyanooximino acetate to form methylcyano dinitroacetate which is then hydrolysed to form dinitroacetonitrile, which in turn is neutralised with an alkali metal hydroxide to form a corresponding alkali metal salt of cyanodinitromethide. The cyanodinitromethide is then saponified with an alkali metal hydroxide in aqueous solution to obtain a corresponding alkali metal salt of dinitromethane.

An object of the present invention is to provide a simpler and less expensive method for preparing alkali metal salts of dinitromethane and other organic as well as inorganic dinitromethane salts.

This is achieved by a method as defined in the claims.

According to the invention, a heterocyclic compound of the general formula

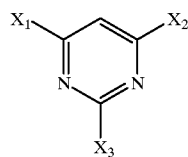

[1]

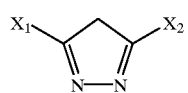

[2]

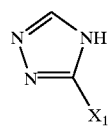

[3]

and tautomers thereof, where $X_1$ and $X_2$ are the same or different and selected from a group consisting of =O, =S, —OH, —SH, halogen, =N—OH, —NH$_2$, —NH—R where R=alkyl and $X_3$ is selected from a group consisting of —H, alkyl, —NO$_2$, =O, =S, —OH, —SH, —N$_3$, —CN, —CNO, —NCO, —CHO, —COOH, —COOR', —C(O)—R', —C(S)—R', —C(O)—S—R', —C(S)—S—R', —C(O)—N(R')—R" where R' and R" are alkyl or aryl, is nitrated with a nitrating agent to form a gem-dinitro compound containing the structural element

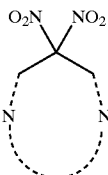

[4]

in the heterocyclic ring structure;

said gem-dinitro compound is hydrolysed in an aqueous medium to split off dinitromethane, and said dinitromethane is neutralised with a neutralising agent to form a corresponding dinitromethane salt.

Suitable starting compounds are e.g.

barbituric acid

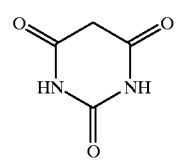

[5]

4,6-dihydroxy-2-methylpynmidine

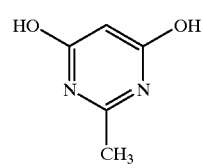

[6]

and
1,2,4-triazol-5-on

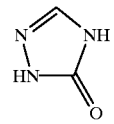

[7]

In nitration use is made of a conventional nitrating system consisting of nitric acid or nitric acid and/or nitrate salts in combination with some other acid. In the first place, nitric acid/sulphuric acid (HNO$_3$/H$_2$SO$_4$) is preferred, but other conceivable nitrating acids are nitric acid/perchioric acid (HNO$_3$/HClO$_4$), nitric acid/phosphoric acid (HNO$_3$/H$_3$PO$_4$), nitric acid/diphosphorus pentoxide (HNO$_3$/P$_2$O$_5$), nitric acid/acetic acid, nitric acid/acetic anhydride, nitric acid/trifluoroacetic acid and nitric acid/trifluoroacetic anhydride.

The nitration is carried out at a low temperature, such as −20−+50° C., and with a moderate acidity of the nitrating system, e.g. 70–100% nitric acid and 70–100% sulphuric acid. Under these circumstances there forms in the reaction mixture a product which contains the structural element [4]. Depending on starting compound and used nitrating acid, temperature and acidity may need be adjusted for an optimal yield of the product. Particularly good results have been achieved with nitric acid (90–100%) and sulphuric acid (90–100%), a temperature of 10–50° C. and a molar ratio of nitric acid to substrate of 2.0–6.0:1, preferably 2.0–3.0:1.

Depending on whether the formed gem-dinitro product [4] is soluble in the nitrating mixture or not, the further process is carried out in slightly different manners.

When the gem-dinitro product [4] forms a precipitate in the nitrating mixture, the product can easily be separated, dissolved in an aqueous medium and hydrolysed with water, optionally after adding a suitable base. In the hydrolysis, dinitromethane is split off, which with an added neutralising agent gives a corresponding dinitromethane salt. For certain starting compounds the product [4] hydrolyses spontaneously and splits off dinitromethane when it is dissolved in water. A second precipitate may then form, which derives from the remaining part of the product [4]. This second precipitate is separated from the aqueous solution before the neutralising agent is added. When adding a base, salts of the dinitromethane ion can be obtained either as dissolved salt or as a solid precipitate depending on the solubility of the formed salts in water. When a precipitate forms, it may easily be separated and, if necessary, be purified by recrystallisation.

Water-soluble dinitromethane salts can, for instance, be separated from the other salts in the mixture by contacting the mixture with an adsorbing agent that adsorbs the dinitromethane salt. Suitable adsorbing agents are activated carbon, silica gel and zeolites. Dinitromethane salts have a higher affinity to these adsorbing agents than, for example, nitrates, sulphates etc. in the neutralised aqueous solution. The adsorption material is suitably arranged in a column through which the aqueous solution is conducted. The dinitromethane salt can then be eluted with hot water and/or a polar organic solvent, such as acetone, 2-propanol, acetonitrile, methanol, ethanol, and be crystallised by evaporation of the eluant.

Free dinitromethane in aqueous solution can also be extracted with a suitable organic solvent, for instance ethyl ether, dichloromethane etc, whereupon the neutralising agent is added to the obtained organic phase for precipitation of a corresponding dinitromethane salt.

In the cases where the product [4] does not precipitate as a solid compound but remains dissolved, the entire nitrating mixture can be diluted with water and, optionally, neutralised to hydrolyse and cleave the product [4]. Subsequently the solution can be acidified with a suitable acid to transform all dinitromethane into the free form, whereupon the dinitromethane is extracted with an organic solvent. The resulting organic phase is then neutralised with a neutralising agent and a corresponding dinitromethane salt precipitates.

An organic or inorganic base is used as the neutralising agent. Suitable neutralising agents that can be used are ammonia $NH_3$, hydrazine $N_2H_4$, a primary amine $RNH_2$, a secondary amine $RR'NH$ or a salt AX, where A is a metal ion or a nitrogen-containing cation and X is a fluoride, chloride, hydroxyl, carbonate, alkoxide or carbonyl ion. R and R' in the amines can be the same or different and constitute alkyl groups having 1–6 carbon atoms.

The respective neutralising reactions can be illustrated by means of the following reaction formulae:

$H_2C(NO_2)_2 + NH_3 \rightarrow NH_4^+ {}^-CH(NO_2)_2$ $H_2C(NO_2)_2 + N_2H_4 \rightarrow N_2H_5^+ {}^-CH(NO_2)_2$ $H_2C(NO_2)_2 + RNH_2 \rightarrow RNH_3^+ {}^-CH(NO_2)_2$ $H_2C(NO_2)_2 + RR'NH \rightarrow RR'NH_2^+ {}^-CH(NO_2)_2$ $H_2C(NO_2)_2 + AX \rightarrow A^+ {}^-CH(NO_2)_2$ Metal ions that may constitute A in the salt AX include mono-, di- or trivalent metal ions which form soluble salts with fluoride, chloride, hydroxyl, carbonate, alkoxide or carbonyl ions. Typical metals include alkali metals Li, Na, K, Rb and Cs; alkaline earth metals Be, Ca, Ba, Sr and Mg; group Ib metals Cu, Ag and Au; group IIb metals Zn, Cd and Hg; group III metals Al, Sc, Y, Ga, In and elements 57–71 of the Lanthanoide series; group IV metals Ti, Zr, Hf, Ge and Sn; group V metals V, Nb, and Ta; group VI metals Cr, Mo and W; group VIIa metals Mn, Tc and Re; and group VIII metals Fe, Co, Ni, Ru, Rh, Pd, Os, Ir and Pt. Preferred metals are Li, Na, K, Be and Mg, especially K.

When A is a nitrogen-containing cation, it may consist of an ion of the formula $(R''_k H_m N_n)^{+z}$, where n=1–8, k=0 to 2+n+z, z=1 to n, m=2+n+z−k and R" is a straight or branched alkyl having 1–6 carbon atoms. Examples of such ions include $NH_4^+$, $CH_3NH_3^+$, $(CH_3)_2NH_2^+$, $(CH_3)_3NH^+$, $(CH_3)_4N^+$, $C_2H_5NH_3^+$, $(C_2H_5)_2NH_2^+$, $(C_2H_5)_3NH^+$, $(C_2H_5)_4N^+$, $(C_2H_5)(CH_3)NH_2^+$, $(C_2H_5)(CH_3)_2NH^+$, $(C_2H_5)_2(CH_3)_2N^+$, $(C_3H_7)_4N^+$, $(C_4H_9)_4N^+$, $N_2H_5^+$, $CH_3N_2H_4^+$, $(CH_3)_2N_2H_3^+$, $(CH_3)_3N_2H_2^+$, $(CH_3)_4N_2H^+$, $(CH_3)_5N_2^+$, etc.

A may also consist of a cubane-1,4bis-ammonium ion, cubane 1,2,4,7-tetraammonium ion; cubane-1,3,5,7-tetraammonium ion; cubane-1,2,3,4-tetraammonium ion; cubane-1,2,3,4,7-pentaammonium ion; cubane-1,2,4,6,8-pentaammonium ion; guanidinium $(C(NH_2)_3^+)$; triaminoguanidinium $(C(N_2H_3)_3^+)$; guanylurea ion $(H_2NC(=NH)NHCONH_3^+)$; nitronium $(NO_2^+)$; nitrosonium $(NO^+)$ or a 1–10000 nitrogen polymer of ethyleneimine.

The invention will be illustrated below by means of examples.

EXAMPLE 1 a) Nitration 6 g barbituric acid [5] was dissolved in 40 ml 95% $H_2SO_4$. Nitric acid (8.5 g 100%) was added. The temperature was kept at about 40° C. A product began to precipitate after 30 min and after 3–4 h it was filtered off. The precipitate was washed with trifluoroacetic acid and dried under vacuum. The yield was 80%. The precipitate consisted of a gem-dinitro compound of the formula

[8]

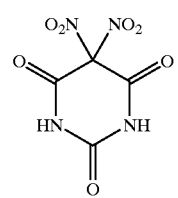

The remaining acid mixture could be reused for renewed nitration by adding additional barbituric acid and optionally a make-up of oleum.

The nitration according to a) was repeated several times at temperatures between 0 and 50° C. and with a smaller excess of nitric acid (down to 3.0 g 100% $HNO_3$). In all cases a precipitate of the gem-dinitro compound [8] was obtained.

b) Neutralisation 3.3 g of the product [8] from the nitration was dissolved in water and ice (30 ml) and the solution was neutralised with a 20% KOH solution. Then the mixture was heated to 80° C. for 2 h. Potassium dinitromethane $(KCH(NO_2)_2$ precipitated in cooling to room temperature and was then recrystallised to purify the salt in respect of sulphates. The yield was 70%. The neutralisation could be monitored by means of UV spectroscopy. The starting material (the gem-dinitro compound [8]) absorbs at 200, 310 and 358 nm and the product, $(KCH(NO_2)_2$, at 363 nm.

EXAMPLE 2

3.0 g of the gem-dinitro compound [8] from nitration according to Example 1 was dissolved in water and ice (30 ml) and the solution was neutralised with a 25% ammonia solution. The mixture was heated to 80° C. for 1.5 h. Ammonium dinitromethane, $NH_4CH(NO_2)_2$, precipitated. The yield was 62%.

EXAMPLE 3

4,6-dihydroxy-2-methylpyrimidine [6](7 g) was dissolved in sulphuric acid (30 ml 95–100%). The temperature of the mixture increased to 40° C. and the mixture was cooled in a water bath to 4° C. Fuming nitric acid (11.8 ml) was then added for 10 min. The temperature of the reaction mixture was during this adding kept at 4–10° C.

The reaction mixture was then allowed to assume room temperature. During the reaction, a precipitate of a gem-dinitro compound formed, and after 2 h the reaction was interrupted by filtering off this precipitate. The precipitate was added to a mixture of 100 g water and 100 g ice during stirring. In connection with the adding gas formed, and a second precipitate formed after one hour. This second precipitate was filtered off and consisted of 1,1-diamino-2,2-dinitroethylene (6.7 g). The filtrate was extracted with 3×60 ml ethyl ether. The ether phase was added to a solution consisting of potassium hydroxide (3 g) in ethanol (50 ml). Potassium dinitromethane then precipitated, was filtered off and recrystallised in 50 ml water. Yield 6.2 g.

What is claimed is:

1. A method of preparing salts of dinitromethane, charactersed by nitration of a heterocyclic compound of the general formula

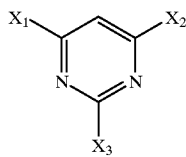

[1]

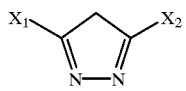

[2]

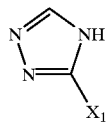

[3]

and tautomers thereof, where $X_1$ and $X_2$ are the same or different and selected from a group consisting of =O, =S, —OH, —SH, halogen, =H—OH, —NH$_2$, —NH—R where R=alkyl and $X_3$, is selected from a group consisting of —H, alkyl, —NO$_2$, =O, =S, —OH, —SH, —N$_3$, —CN, —CNO, —NCO, —CHO, —COOH, —COOR', —C(O)—R', —C(S)—R', —C(O)—S—R', —C(S)—S—R', —C(O)—N(R')—R" where R' and R" are alkyl or aryl, with a nitrating agent to form a gem-dinitro compound containing the structural element

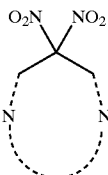

[4]

in the heterocyclic ring structure;

hydrolysation of said gem-dinitro compound in an aqueous medium to split off dinitromethane, and neutralisation of said dinitromethane with a neutralising agent to form a corresponding dinitromethane salt.

2. A method as claimed in claim 1, characterised in that the heterocyclic compound is barbituric acid.

3. A method as claimed in claim 1, characterised in that the heterocyclic compound is 4,6-dihydroxy-2-methylpyrimidine.

4. A method as claimed in claim 1, characterised in that the heterocyclic compound is trazolone.

5. A method as claimed in claim 1, characterised in that the nitrating agent is selected from a group consisting of nitric acid, nitric acid/sulphuric acid ($HNO_3/H_2SO_4$), nitric acid/perchloric acid ($HNO_3/HClO_4$), nitric acid/phosphoric acid ($HNO_3/H_3PO_4$), nitric acid/diphosphorus pentoxide ($HNO_3/P_2O_5$), nitric acid/acetic acid, nitric acid/acetic anhydride, nitric acid/trifluoroacetic acid and nitric acid/trifluoroacetic anhydride.

6. A method as claimed in claim 1, characterised in that the nitration is carried out at a temperature of −20–+50° C.

7. A method as claimed in claim 1, characterised in that said dinitromethane is extracted from the aqueous medium with an organic solvent, and that said neutralisation is carried out in the organic solvent.

8. A method as claimed in claim 7, characterised in that the organic solvent is ethyl ether.

9. A method as claimed in claim 1, characterised in that the neutralisation is carried out in aqueous solution, and that the dinitromethane salt is separated from said aqueous solution by means of an adsorbing agent that adsorbs the dinitromethane salt.

10. A method as claimed in claim 9, characterised in that the adsorbing agent is selected from a group consisting of activated carbon, silica gel and zeolites.

11. A method as claimed in claim 1, characterised in that said neutralising agent is selected from a group consisting of ammonia, hydrazine, a primary amine of the formula $RNH_2$, a secondary amine of the formula RR'NH and a salt of the formula AX, where R and R' are the same or different alkyl groups having 1–6 carbon atoms and A is a metal cation or a nitrogen-containing cation and X is an anion selected from a group consisting of fluoride, chloride, hydroxyl, carbonate, alkoxide and carboxyl.

12. A method as claimed in claim 11, characterised in that the neutralising agent is an alkali metal hydroxide or an alkaline earth metal hydroxide.

13. A method as claimed in claim 12, characterised in that the alkali metal hydroxide is potassium hydroxide.

* * * * *